United States Patent [19]

Nissen et al.

[11] 4,133,836

[45] Jan. 9, 1979

[54] MANUFACTURE OF ACETALS

[75] Inventors: Axel Nissen, Leimen; Gerd Kaibel, Lampertheim, both of Fed. Rep. of Germany

[73] Assignee: BASF Aktiengesellschaft, Ludwigshafen, Fed. Rep. of Germany

[21] Appl. No.: 801,561

[22] Filed: May 31, 1977

[30] Foreign Application Priority Data

Jun. 4, 1976 [DE] Fed. Rep. of Germany ....... 2625074
Apr. 1, 1977 [DE] Fed. Rep. of Germany ....... 2714590

[51] Int. Cl.$^2$ ............................................. C07C 41/00
[52] U.S. Cl. ................................. 568/596; 560/126; 560/183; 560/238; 560/262; 568/598; 568/591
[58] Field of Search ................... 260/615 A; 560/238, 560/262, 126, 183

[56] References Cited

U.S. PATENT DOCUMENTS

| | | | |
|---|---|---|---|
| 2,573,678 | 11/1951 | Saunder | 262/615 A X |
| 2,691,049 | 10/1954 | Thomas | 260/615 A |
| 2,800,513 | 7/1957 | Hall et al. | 260/615 A |
| 2,848,500 | 8/1958 | Funck | 260/615 A X |
| 3,819,720 | 6/1974 | Kliegman | 260/615 A |
| 3,978,092 | 8/1976 | Ichikawa et al. | 260/615 A |

FOREIGN PATENT DOCUMENTS 121443  10/1958  U.S.S.R. ............................. 260/615 A

OTHER PUBLICATIONS

Vinokurov, Gidrolizi Lesokhim, Prom. 12 No. 5 4–6 (1959).

Primary Examiner—Howard T. Mars
Attorney, Agent, or Firm—Keil, Thompson & Shurtleff

[57] ABSTRACT

A process for the manufacture of acetals by reacting aliphatic aldehydes with aliphatic alcohols, especially olefinically unsaturated aldehydes and allyl alcohols, in the presence of a distillable acid, especially nitric acid, using a rectifying column as the reaction vessel. The products may be used as starting materials for plastics, active substances, scents and vitamins.

6 Claims, No Drawings

MANUFACTURE OF ACETALS

The present invention relates to a process for the manufacture of acetals by reacting aliphatic aldehydes with aliphatic alcohols in the presence of distillable acids, especially nitric acid, in a rectifying column as the reaction vessel.

If the aldehydes and alcohols to be used for the manufacture of the acetals are industrially readily accessible, the direct acetalization of aldehydes in the presence of acid catalysts, in accordance with the equation given below, is the simplest industrial method for obtaining the acetals:

The problem presented by this reaction is that an equilibrium between the starting compounds and the end products is set up. Higher conversions are therefore only achieved if at least one of the reaction products, e.g., the water, is removed from the reaction mixture.

Various methods for removing the water, formed by direct acetalization, from the reaction mixture have been disclosed. For example, according to German Laid-Open Application DOS No. 2,411,530, dehydrating auxiliary chemicals, e.g., molecular sieves or calcium sulfate, are used for this purpose. In this process, the molecular sieves are employed in amounts of 20-45% by weight, based on the starting compounds; calcium sulfate is even employed in amounts of up to 90% by weight. Auxiliary chemicals which are used in such amounts, based on the reactants, and which furthermore do not give a homogeneous solution, make it difficult to carry out the process industrially, especially if, for cost reasons, it is necessary to regenerate them. Even if this expensive procedure is employed, the process does not give satisfactory yields.

The long reaction times are a further substantial disadvantage of the process of German Laid-Open Application DOS No. 2,411,530. For example, the acetalization requires 72 hours in Example 4 and 100 hours in Example 13. The resulting poor space-time yields are undesirable in industrial practice.

In addition to molecular sieves and calcium sulfate, German Laid-Open Application DOS No. 2,411,530 names ammonium nitrate as a preferred catalyst. However, the latter results in significantly poorer selectivities than those obtained with molecular sieves and calcium sulfate.

A further possible method of removing the water formed during direct acetalization is to employ azeotropic distillation with an inert entraining agent. For example, according to German Laid-Open Application DOS No. 2,423,409 the water formed by the acetalization is removed from the reaction mixture by azeotropic distillation with n-heptane (Example 2). The process of German Laid-Open Application DOS No. 2,423,409 has the advantage over the process of German Laid-Open Application DOS No. 2,411,530 that the auxiliary chemical, namely n-heptane, is easier to handle in industrial operation than the solids mentioned above. However, the fact that the reactants are diluted with about 75% by weight of heptane, and that the reaction times are long (15 hours in Example 2; the conversion is not disclosed) is a disadvantage, because of the high investment required and the high heating costs.

A further disadvantage of the process of German Laid-Open Application DOS No. 2,423,409 is the poor selectivity. In Example 2, only 37.7 parts of distillable product are formed from a total of 59 parts of starting compounds, and of these 37.7 parts only 7.2 parts consist of the desired acetal. Catalysts recommended for this process are acid compounds, e.g., ammonium sulfate, ammonium nitrate, boric acid and others.

S. Julia et al., Bull. Soc. Chim. France 1962, pages 1960–68 recommend benzene as an inert entraining agent in the manufacture of 1,1-bis-(prop-2-en-1-yloxy)-but-2-ene. This process gives a yield of only 32.5% of acetal, based on crotonaldehyde, after 24 hours' reaction time. The same authors describe the synthesis of 1,1-bis-(2-methyl-prop-2-en-1-yloxy)-but-2-ene without added entraining agent. In that case, only 20% of acetal, based on crotonaldehyde, are obtained after a reaction time of 17.5 hours.

It is an object of the present invention to provide a process which makes it possible to carry out the acetalization of aldehydes with alcohols, especially the acetalization of sensitive $\alpha,\beta$-unsaturated aldehydes, in a technically simple manner, with good conversions and good selectivities.

We have found, surprisingly, that this object is achieved and that aldehydes, especially the sensitive $\alpha,\beta$-unsaturated aldehydes, can be acetalized in a simple manner, and with good selectivities, by reaction with alcohols in the presence of an acid, if the reaction of the aldehyde with the alcohol is carried out in the presence of distillable acids, especially nitric acid, in a rectifying column, provided at the top with a device for discharging water, as the reaction vessel.

Further, we have found that this process is particularly successful if the distillable acid used boils below 200° C. and is employed in an amount of from $1 \times 10^{-6}$ to 10% by weight (calculated as 100% strength acid), based on the mixture of aldehyde and alcohol.

It is particularly advantageous to carry out the process of the invention in a rectifying column with up to 80 theoretical plates.

In all embodiments of the process, nitric acid has proved best; it is preferably employed in amounts of from $1 \times 10^{-6}$ to 1% by weight, based on the reaction mixture.

The process of the invention offers particular advantages for the manufacture of acetals of the general formula I

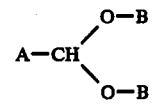

where A is one of the radicals $R^1 - CR = CR -$, $R^1 - CHR - CHR -$ or $CH_2 = CR - CHR -$ and the B's are identical or different radicals of the type $- CRR - CR = CR - R^2$, $- CRR - CHR - CHR - R^2$ or $- CRR - CHR - CR = CH_2$, where the R's are identical or different and each is hydrogen or alkyl of 1 to 4 carbon atoms, $R^1$ is hydrogen or alkyl of 1 to 4 carbon atoms which may in turn be substituted by alkoxy of 1 to 4 carbon atoms or by alkoxycarbonyl (where alkoxy is of 1 to 4 carbon atoms), and $R^2$ is hydrogen or an aliphatic, aliphatic-cycloaliphatic or cycloaliphatic hydrocarbon radical of up to 12 carbons atoms which may contain up to 4 carbon-carbon double bonds, which is carried out by reacting 1 molar proportion of an aldehyde or aldehyde mixture of the general formula II $$A - CHO \quad \text{II}$$

with at least 2 molar proportions of an alcohol or alcohol mixture of the general formula III $$HO - B \quad \text{III}$$

The process of the invention is superior to conventional methods of acetalization, above all in cases in which one of the components II or III or both are mono- or poly-olefinically unsaturated, since the unsaturated alcohols and aldehydes, especially the $\alpha,\beta$-unsaturated aldehydes and allyl alcohols, are particularly sensitive to undesirable side-reactions.

Examples of aldehydes of the formula II which may be employed according to the invention are acrolein, but-2-en-1-al, 2-methyl-but-2-en-1-al, 3-methyl-but-2-en-1-al, 2-methyl-4-methoxy-but-2-en-1-al, 2-methyl-4-acetoxy-but-2-en-1-al, 3-isopropyl-but-2-en-1-al and 3-methyl-but-3-en-1-al, preferably 3-methyl-but-2-en-1-al. In addition, the corresponding saturated compounds may also be used, i.e., propionaldehyde, n-butyraldehyde, 2-methyl-butan-1-al, 3-methyl-butan-1-al, 2-methyl-4-methoxy-butan-1-al, 2-methyl-4-acetoxy-butan-1-al and 3-isopropyl-butan-1-al.

Examples of unsaturated alcohols of the formula III suitable for use according to the invention are prop-2-en-1-ol, but-2-en-1-ol, 2-methyl-but-3-en-2-ol, 3-methyl-but-3-en-1-ol, geraniol, 2-methyl-prop-2-en-1-ol, 3-methyl-but-2-en-1-ol and especially 3-methyl-but-2-en-1-ol.

Propan-2-ol, propan-2-ol, butan-1-ol, 2-methyl-butan-1-ol, 3-methyl-butan-1-ol and isobutanol may be mentioned as corresponding saturated alcohols, In principle, it is desirable to manufacture acetals I which are single compounds, so that single aldehydes I and alcohols II are used as starting materials.

Frequently, the manufacture of the aldehydes II or of the alcohols III results in mixtures instead of the pure saturated or unsaturated compounds. If these mixtures are employed, the corresponding mixtures of the various possible acetals are obtained, which in some cases can be used just as well for further syntheses as can the individual acetals. For example, in the manufacture of 3-methyl-but-2-en-1-ol from 3-methyl-but-3-en-1-ol in accordance with German Published Application DAS 1,901,709, mixtures of these two alcohols in about equal parts may be formed. These mixtures can, according to the process of the invention, advantageously be converted, by reaction wtih 3-methyl-but-2-en-1-al or 3-methyl-but-3-en-1-al, into the corresponding mixtures of acetals which can be used further, as such, for the manufacture of citral.

The difference in boiling points of the compounds II and III is not critical but should advantageously not exceed 100° C. and preferably not exceed 50° C. The following may be mentioned as examples of distillable acids having a boiling point below 200° C.: nitric acid, perchloric acid, hydrohalic acids, haloacetic acids, acetic acid, propionic acid, butyric acid, iso-butyric acid, valeric acid and acrylic acid, especially nitric acid.

When using stronger acids, e.g., nitric acid, perchloric acid, hydrohalic acids and haloacetic acids, smaller amounts of catalyst acid are normally used, i.e., from about $1 \times 10^{-6}$ to 1% by weight, based on the starting material, whilst when using weaker acids such as acetic acid, propionic acid, butyric acid, iso-butyric acid, valeric acid and acrylic acid as the catalyst acid, such acids are generally employed in somewhat larger amounts, i.e., up to 10% by weight based on the starting material, since the reaction times required are otherwise very long.

The stronger acids are preferred catalysts, since, though they are employed in smaller amounts, shorter reaction times suffice to achieve quantitative conversion. The process according to the invention proves very particularly advantageous when nitric acid is used as the catalyst. This preferred catalyst can be employed either in the form of fuming nitric acid, i.e., almost pure, about 98% strength, $HNO_3$, or in the form of aqueous $HNO_3$ solutions. It is advantageous to use commercial concentrated nitric acid, i.e., about 69% strength aqueous $HNO_3$ solution of constant boiling point. However, dilute aqueous nitric acid can also be used under the conditions according to the invention, since the water used for dilution is removed from the reaction mixture, during the reaction, by distillation together with the water formed in the reaction.

In general, it is advantageous to dilute the nitric acid with the alcohol III to be reacted, and introduce it in this form into the reaction vessel. This is particularly advisable when using fuming nitric acid.

It is very surprising that nitric acid can be used advantageously as a catalyst for the acetalization of the $\alpha,\beta$-unaldehydes, which are known to oxidize and polymerize readily. As early a publication as "Organikum" 9th edition, VEB Deutscher Verlag der Wissenschaften, Berlin 1959, page 430, states that when acetalizing $\alpha,\beta$-unsaturated carbonyl compounds specific conditions must be observed since the alcohol can easily undergo adduct formation at the reactive activated double bond. The use of $NH_4NO_3$ is recommended. In none of the above processes for acetalizing $\alpha,\beta$-unsaturated aldehydes is nitric acid mentioned as a possible acid catalyst. According to the process of German Laid-Open Application DOS No. 2,411,530, the use of the ammonium salt of nitric acid as the acid catalyst results in substantially poorer selectivities in the manufacture of acetals of the formula I than when calcium sulfate or molecular sieves are used. In the process of German Laid-Open Application DOS No. 2,439,140 for acetalizing $\beta,\gamma$-unsaturated aldehydes, i.e., aldehydes in which there is no mutual activation of the double bonds and the carbonyl group, nitric acid is mentioned as a possible catalyst amongst innumerable other acid compounds.

It is essential, in the process according to the invention, that the reaction of the aldehyde with the alcohol is carried out under rectifying conditions so that the starting compounds and the nitric acid are in the main part of the rectifying column, water is discharged at the top of the column and the acetal formed is taken off at the bottom of the column. The apparatus used is a rectifying column, suitably one with from about 1 to 80, especially from 5 to 35, theoretical distillation plates. In industrial operation, any design of rectifying column can be used, i.e., the design is not critical. For example, it is possible to use tray columns, e.g., bubble-cap tray columns, sieve tray columns, valve tray columns, tunnel tray columns, dual-flow tray columns and centrifugal tray columns, packed columns with Pall rings, Raschig rings, Berl saddles, gauze rings, wire spirals or others as the packings, columns with gauze packing (e.g., of the Sulzer or Montz type), trickle-film columns, grid tray columns and others. A device is provided at the top of the column for discharging the water of reaction. Advantageously, a phase separating vessel and/or a proportioning reflux device is used.

In carrying out the reaction according to the invention it is in most cases feasible and particularly advantageous to remove the water essentially only with the aid of the starting compounds. However, in principle it is possible, and in some cases advantageous, to remove the water, in the reaction according to the invention, by means of an inert entraining agent which has a lower boiling point than the starting compounds and which is used in such small amounts that during the reaction it is only present in the uppermost part of the column, i.e. that the starting compounds of the formulae II and III are not displaced from the main part of the column. For the purposes of the invention, the uppermost part of the column means the part of the column, below the column top, which is the minimum section required to separate the entraining agent from the reactants. It is clear from this that it is advantageous to have a good separation, i.e. a sufficiently large difference between the boiling points of the reactants and that of the entraining agent, if the column available has only a limited number of theoretical distillation plates.

Removing the water with the aid of an inert entraining agent at the top of the column is particularly advantageous if the lower-boiling starting component does not exhibit a miscibility gap with water under the conditions prevailing at the top of the column, as is the case, for example, with allyl alcohol.

Suitable inert entraining agents are all compounds which undergo no change under the reaction conditions, which furthermore, in the pure state or in the presence of water, boil at a lower temperature than the starting compounds, and which may or may not exhibit a miscibility gap with water in the liquid phase, examples of such compounds being hydrocarbons, e.g., pentane, hexane, cyclohexane and benzene, halohydrocarbons, e.g., methylene chloride, and ethers, e.g., dipropyl ether.

The process of the invention may be carried out continuously or batchwise.

To carry out the continuous process, the reaction feed, consisting of the aldehyde or aldehyde mixture of the formula II, an alcohol or alcohol mixture of the formula III and nitric acid, is in general introduced at any point of the column and the heating of the column is regulated so that the temperature at the level of the lowest theoretical distillation plates does not exceed 140° C., preferably 100° C. The feed point is not critical. However, depending on the boiling characteristics of the reactants, it may be of advantage to select a feed point in the upper or lower half of the column. For example, for the reaction of 3-methyl-but-2-en-1-al with 3-methyl-but-2-en-1-ol, a feed point in the upper half of the column is advantageous. Under these conditions, the acetal of the formula I can be taken off as a crude product from the lower part or the bottom of the column.

This crude product in general no longer contains any more of the aldehyde of the formula II, which is frequently employed in less than equivalent amount; conversely, the alcohol of the formula III is frequently employed in excess and the crude product contains an amount corresponding to this excess. It may be seen from this that in continuous operation it is advisable to keep the excess of starting alcohol as low as possible. After removing the excess alcohol by distillation, the product is sufficiently pure that any further distillation of the acetals of the formula I can be dispensed with. The product contains more than 98% of the desired acetal or acetal mixture and can be used in this form for further reactions.

To carry out the batchwise process, the starting compounds, including nitric acid, are introduced into the column still and the reaction mixture is boiled until no further water is discharged from the water separator at the top of the column. It is however also possible to introduce the catalyst, appropriately diluted, separately from the reactants at the top of the column. The conversion, based on the aldehyde of the formula II, which is generally employed in less than equivalent amount, is then again quantitative. The distillation bottom corresponds to that obtained in continuous operation. The reaction temperatures are in general from about 0 to 140° C., especially from about 15 to 100° C., the temperature gradient from the bottom to the top of the column being in most cases from 20 to 80° C. The temperatures in the rectifying column can be varied by altering the pressure. The column can therefore be operated under reduced pressure, normal pressure or superatmospheric pressure. The pressure chosen depends on the temperatures appropriate to the reaction. For example, the reaction of 3-methyl-but-2-en-1-al with 3-methyl-but-2-en-1-ol is preferably carried out under pressures of from about 2 to 200 mm Hg. The pressure in itself has no effect on how successfully the reaction proceeds, even though the reaction takes place in a system comprising a gas phase and a liquid phase.

In batchwise operation, the reaction time to achieve quantitative conversion is from 1 to 6 hours with heat inputs corresponding to from about 0.5 to 4 units of column reflux per unit of acetal formed.

In continuous operation, the heat input for quantitative conversion is again from about 0.5 to 8 units of column reflux per unit of acetal formed.

From 2 to 30, preferably from 2 to 6, moles of the alcohol of the formula III are used per mole of aldehyde of the formula II. The distillable acids are in general used in amounts of from about $1 \times 10^{-6}$ to 10% by weight. Nitric acid, which is used preferentially, is advantageously employed in amounts of from $1 \times 10^{-6}$ to 1% by weight, based on the starting material and calculated as 100% strength $HNO_3$, preferably from $1 \times 10^{-4}$ to $1 \times 10^{-2}$% by weight.

Using the process according to the invention, the acetals of the formula I can be manufactured without addition of auxiliary chemicals which are expensive and/or troublesome to handle in industrial operation, e.g., molecular sieves, calcium sulfate or even n-heptane, the reaction times are substantially shorter than in conventional processes, the conversion of the aldehyde component is virtually quantitative, and the selectivity is in most cases above 97%, based on both starting components, selectivity in this context meaning the yield based on material converted.

The acetals manufactured by the process of the invention may be used as starting materials for plastics, active substances, scents and vitamins. For example, 1,1-bis-(3-methyl-but-2-en-1-yloxy)-3-methyl-but-2-ene, obtainable from 3-methyl-but-2-en-1-al and 3-methyl-but-2-en-1-ol, is an important starting compound for the manufacture of vitamins A and E.

EXAMPLE 1

690 g (8.2 moles) of 3-methyl-but-2-en-1-al, 1730 g (20 moles) of 3-methyl-but-2-en-1-ol and 23 mg of 65% strength nitric acid (corresponding to $0.62 \times 10^{-4}$% by weight of 100% strength $HNO_3$, based on 2,420 g of starting compounds) are boiled under 60 mm Hg in a 4 liter flask surmounted by a packed column (filled with 5 mm Raschig rings). The bottom temperature assumes a value of 76–88° C. The packed column has a diameter of 45 mm and has 30 theoretical plates. The water formed in the reaction is taken off at the top of the column and the organic material which separates from the water is returned continuously into the top of the column. With a reflux of 600 g/hour, quantitative conversion of the aldehyde is achieved after 4.5 hours. 1,1-Bis-(3-methyl-but-2-en-1-yl-oxy)-3-methyl-but-2-ene is obtained about 99% pure after distilling off the excess alcohol, the yield being 98.6% based on 3-methyl-but-2-en-1-al and 98.2% based on 3-methyl-but-2-en-1-ol.

EXAMPLE 2

A feed consisting of 25% by weight of 3-methyl-but-2-en-1-al and 75% by weight of 3-methyl-but-2-en-1-ol together with $1 \times 10^{-2}$% by weight of nitric acid (calculated as 100% strength acid, but employed in the form of a 65% strength nitric acid) is introduced at the rate of 300 units per hour, at the level of the 6th theoretical plate from the top, into a column with 22 theoretical plates, equipped with a gauze packing, water separator and falling film evaporator, the reflux being 310 units per hour. The pressure at the top of the column is 75 mm Hg, which results in a temperature of 78° C. at the lowest theoretical plate of the column. The crude product is taken off continuously at the lower end of the falling film evaporator. Under these reaction conditions, a conversion of 97%, based on 3-methyl-but-2-en-1-al, is achieved. The selectivity is more than 98%, based on either starting component. The acetal (1,1-bis-(3-methyl-but-2-en-1-yloxy)-3-methyl-but-2-ene) can be isolated in 98% purity by distilling off the unconverted starting materials.

EXAMPLE 3

If the procedure described in Example 2 is followed but the starting mixture is run in at the level of the 10th theoretical plate from the top, and cyclohexane is pumped into the column by means of a second pump, at the beginning of the experiment, until a marked temperature change from about 50 to about 25° C. between the 3rd and 6th theoretical plates from the top indicates that the uppermost part of the column is filled with cyclohexane, the acetal (1,1-bis-(3-methyl-but-2-en-1-yloxy)-3-methyl-but-2-ene) is obtained, at about the same heat input, with about the same selectivity and purity as in Example 2.

EXAMPLE 4

A feed consisting of 12% by weight of 3-methyl-but-2-en-1-al and 78% by weight of 3,7-dimethyl-2,6-octadien-1-ol together with $7 \times 10^{-3}$% by weight of nitric acid (calculated as 100% strength acid, but employed in the form of a 20% strength aqueous nitric acid) is introduced at the rate of 25 units per hour, at the level of the 1st theoretical plate from the top, into a column with 10 theoretical plates, equipped with a gauze packing, water separator, condenser and falling film evaporator, the reflux being 100 units per hour. The pressure at the top of the column is 2 mm Hg, resulting in a top temperature of 4° C. and a temperature of 97° C. at the lowest theoretical plate. The condenser is operated with a medium kept at a constant temperature of 0° C. The crude product is taken off continuously at the lower end of the falling film evaporator. Under the reaction conditions described, a conversion of 94.5%, based on 3-methyl-but-2-en-1-al, is achieved. The selectivity for 1,1-bis-(3,7-dimethyl-octa-2,6-dien-1-yloxy)-3-methyl-but-2-ene is about 98% of theory, based on both starting components.

EXAMPLE 5

46 units per hour of a feed consisting of 18.7% by weight of 3-methyl-4-acetoxy-but-2-en-1-al and 81.3% by weight of 3,7-dimethyl-octa-2,6-dien-1-ol as well as $4 \times 10^{-3}$% by weight of nitric acid (calculated as 100% strength acid) are introduced into the column described in Example 4, at the level of the 1st theoretical plate from the top, and the reaction is carried out at a heat input corresponding to 110 units of reflux per hour. The temperature at the column top is 54° C. At a conversion of 98%, based on 3-methyl-4-acetoxy-but-2en-1-al, a selectivity of 89%, based on 3-methyl-4-acetoxy-but-2-ene and a selectivity of 96%, based on 3,7-dimethyl-octa-2,6-dien-1-ol, is achieved.

EXAMPLE 6

500 g of 3-methyl-but-2-en-1-al, 2,500 g of 3-methyl-but-2-en-1-ol and 60 g of isobutyric acid are reacted in the apparatus described in Example 1, at a reflux rate of 600 g/hour. After 26 hours, quantitative conversion of the 3-methyl-but-2-en-1-ol is achieved. The selectivities for 1,1-bis(3-methyl-but-2-en-1-yloxy)-3-methyl-but-2-ene are 98%, based on 3-methyl-but-2-en-1-al and 93%, based on 3-methyl-but-2-en-1-ol.

EXAMPLES 7 TO 14

1 mole of an aldehyde or aldehyde mixture II and a moles of an alcohol or an alcohol mixture III are acetalized in the presence of b % by weight (based on the amount of aldehyde and alcohol) of nitric acid in the form of a 65% strength aqueous solution at a bottom temperature of T° C. under p mm Hg in the course of t hours, in a reaction vessel surmounted by a packed column possessing 30 theoretical plates, the water formed being removed continuously from the reaction mixture. The acetals 1 formed are then isolated by distillation in the conventional manner. Where mixtures of unsaturated alcohols and the corresponding saturated alcohols are used, the ratio of the 3 acetals formed is determined by gas chromatography or NMR spectroscopy. Based on a conversion of U %, the yield of the desired acetals is q %. If several acetals are formed, their percentage by weight of the total reaction product is indicated.

The reaction conditions, and the results of the individual Examples, are listed in the Table which follows.

| Example No. | 1 [mole] of aldehyde a [moles] of alcohol | | b [% by weight] HNO₃ | T (bottom) [°C] | t [h] | p [mm Hg] | Acetal IV | Conversion U [%] | Yield q [%] | Boiling point [°C/mm Hg] |
|---|---|---|---|---|---|---|---|---|---|---|
| 7 | 1 mole | 3-methyl-butan-1-al | $4.1 \times 10^{-3}$ | 58–85 | 8 | 64 | 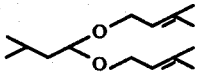 | 60 | 92 | 97/0.2 |
| | 3.8 moles | 3-methyl-but-2-en-1-ol | | | | | | | | |
| 8 | 1 mole | 3-methyl-but-2-en-1-al | $4.0 \times 10^{-3}$ | 65–87 | 10 | 60 | 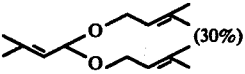 (30%)<br>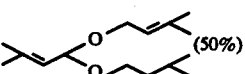 (50%)<br>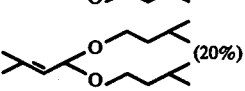 (20%) | 100 | 94 | 94/0.2 for the mixture |
| | 2.0 moles | 3-methyl-but-2-en-1-ol | | | | | | | | |
| | 2.0 moles | 2-methyl-butan-1-ol | | | | | | | | |
| 9 | 1 mole | 3-methyl-but-2-en-1-al | | | | | 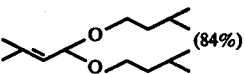 (84%) | | | |
| | 1 mole | 3-methyl-butan-1-al | $2.1 \times 10^{-3}$ | 70–82 | 5 | 60 | | 63 | 98 | 100/0.5 for the mixture |
| | 4 moles | 3-methyl-but-2-en-1-ol | | | | | 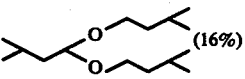 (16%) | | | |
| 10 | 1 mole | butanal | $3.9 \times 10^{-3}$ | 97–104 | | 760 | 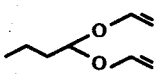 | 66 | 90 | 33/3 |
| | 4 moles | prop-2-en-1-ol | | | | | | | | |
| 11 | 1 mole | butanal | $3.9 \times 10^{-3}$ | 55–90 | 10 | 760 | 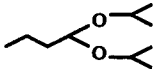 | 40 | 92 | 37/3 |
| | 4 moles | isopropanol | | | | | | | | |
| 12 | 1 mole | 2-methyl-propanal | $3.9 \times 10^{-3}$ | 103–105 | 12 | 760 | 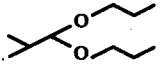 | 56 | 87 | 33/3 |
| | 4 moles | n-propanol | | | | | | | | |
| 13 | 1 mole | butanal | $3.9 \times 10^{-3}$ | 94–100 | 10 | 760 | 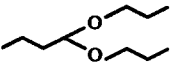 | 61 | 97 | 76/17 |
| | 4 moles | n-propanol | | | | | | | | |
| 14 | 1 mole | 3-methyl-but-2-en-1-al | $2 \times 10^{-3}$ | 68–79 | 6 | 60 | 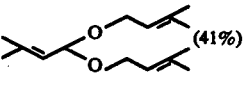 (41%)<br>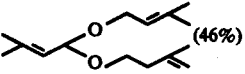 (46%)<br>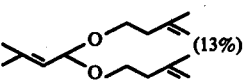 (13%) | 55 | 95 | |
| | 2 moles | 3-methyl-but-2-en-1-ol | | | | | | | | |
| | 2 moles | 3-methyl-but-3-en-1-ol | | | | | | | | |

EXAMPLE 15

700 g of a mixture containing 90.2% by weight of 3-methyl-but-3-en-1-al and 5.3% by weight of 3-methyl-but-2-en-1-al, 2,780 g of 3-methyl-but-2-en-1-ol and 6 g of 51% strength aqueous nitric acid are boiled under 100 mm Hg in a 4 liter flask surmounted by a packed column (filled with 5 mm Raschig rings). The bottom temperature assumes a value of from 86 to 93° C. The column has a diameter of 45 mm and has 30 theoretical plates. The water formed in the reaction is taken off at the top of the column and the organic materials which separates from the water is returned continuously into the column. With a reflux of 600 g/hour, quantitative conversion of the aldehyde is achieved in 16 hours. After distilling off the excess alcohol, a mixture consisting of 74.5% by weight of 1,1-bis-(3-methyl-but-2-en-1-yloxy)-3-methyl-but-3-ene and 10.6% by weight of 1,1-bis-(3-methyl-but-2-en-1-yloxy)-3-methyl-but-2-ene, together with the by-products 3-methyl-butadien-1-yl-3-methyl-but-2-en-1-yl-ether (5.9% by weight) and di-(3-methyl-but-2-en-1-yl)-ether is obtained. The selectivity of the acetals obtained is 86.5% based on the sum of the aldehydes employed and 72.5% based on 3-methyl-but-2-en-1-ol.

We claim:

1. In a process for the manufacture of an acetal of the formula

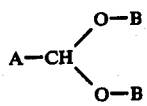

where A is one of the radicals $R^1 - CR = CR -$ or $CH_2 = CR - CHR -$ and B is one of the radicals $-CRR - CR = CR - R^2$ or $-CRR - CHR - CR = CH_2$, wherein:

R is hydrogen or alkyl of 1 to 4 carbon atoms;
$R^1$ is hydrogen, alkyl of 1 to 4 carbon atoms or said alkyl substituted by alkoxy of 1 to 4 carbon atoms; and
$R^2$ is hydrogen or an aliphatic, aliphatic-cycloaliphatic or cycloaliphatic hydrocarbon radical of up to 12 carbon atoms which is saturated or contains up to 4 carbon-carbon double bonds, by reacting 1 molar proportion of an unsaturated aldehyde or aldehyde mixture of the formula

A — CHO      II with at least 2 molar proportions of an unsaturated alcohol or alcohol mixture of the formula

HO — B      III,

A and B having the meanings set forth above, in the presence of an acid acetalization catalyst, the improvement which comprises:
carrying out the reaction in the presence of nitric acid as the essential acetalization catalyst under rectifying conditions so that the starting compounds and the nitric acid during the reaction are in the main part of the rectifying column;
discharging water at the top of the column; and taking off the acetal formed at the bottom of the column.

2. A process as claimed in claim 1, wherein the nitric acid is employed in an amount of from $1 \times 10^{-6}$ to 1% by weight (calculated as 100% strength acid), based on the mixture of aldehyde and alcohol.

3. A process as claimed in claim 1, wherein an $\alpha,\beta$-unsaturated aldehyde I is reacted with an allyl alcohol II.

4. A process as claimed in claim 1, wherein 3-methyl-but-2-en-1-al is used as the aldehyde of the formula II and is reacted with an alcohol of the formula III.

5. A process as claimed in claim 1, wherein 3-methyl-but-2-en-1-ol is used as the alcohol of the formula III and is reacted with an aldehyde of the formula II.

6. A process as claimed in claim 1, wherein 3-methyl-but-2-en-1-al, as the aldehyde of the formula II, is reacted with 3-methyl-but-2-en-1-ol, as the alcohol of the formula III, to give 1,1-bis-(3-methyl-but-2-en-1-yloxy)-3-methyl-but-2-ene.

* * * * *